United States Patent [19]

Palmer

[11] Patent Number: 4,638,539
[45] Date of Patent: Jan. 27, 1987

[54] ASPIRATING/VENTILATING APPARATUS AND METHOD

[75] Inventor: Darrel Palmer, Sandy, Utah

[73] Assignee: Ballard Medical Products, Midvale, Utah

[21] Appl. No.: 767,400

[22] Filed: Aug. 20, 1985

Related U.S. Application Data

[62] Division of Ser. No. 633,570, Jul. 23, 1984, Pat. No. 4,569,344.

[51] Int. Cl.$^4$ .............................................. B21D 53/00
[52] U.S. Cl. ..................................... 29/157 R; 29/450; 29/469; 128/207.16; 604/171
[58] Field of Search ...................... 29/157 R, 450, 469; 128/207.14, 207.16; 137/533.17; 251/95, 100; 604/163, 171, 173

[56] References Cited

U.S. PATENT DOCUMENTS 4,122,591 10/1978 Kramann et al. .................. 29/157 R
4,225,371  9/1980 Taylor et al. ..................... 29/157 R X
4,356,610 11/1982 Hon et al. ............................ 29/157 R Primary Examiner—Mark Rosenbaum
Assistant Examiner—Ronald S. Wallace
Attorney, Agent, or Firm—Lynn G. Foster

[57] ABSTRACT

A ventilating and aspirating assembly comprising an aspirating catheter tube internally disposed within and coextensive with a surrounding flexible collapsible sterility preserving film envelope, a connector by which ventilating air is involuntarily delivered to and exhausted from the lungs of a medical patient, said connector comprising structure which accommodates the manual insertion of the catheter tube into and manual removal from the trachea/bronchi patient through the connector. This facilitates aspiration of undesired respiratory fluids. The assembly further comprises a detachable connection site for one end of the envelope to the connector and a valve by which aspirating vacuum pressure is selectively communicated to the interior of the catheter tube for evacuation of said respiratory fluids, the valve comprising structure isolating the vacuum pressure from the atmosphere, structure by which the valve is placed in either of a locked and an unlocked condition and structure normally biasing and sealing the valve in a closed position, but accommodating manual displacement counter to the bias into an unsealed open position whereby, with the catheter tube indwelling in the lungs of the patient, the vacuum pressure causes evacuation of fluid from the patient's respiratory system through the catheter tube, and a detachable connection site for the other end of the envelope to the valve.

1 Claim, 12 Drawing Figures

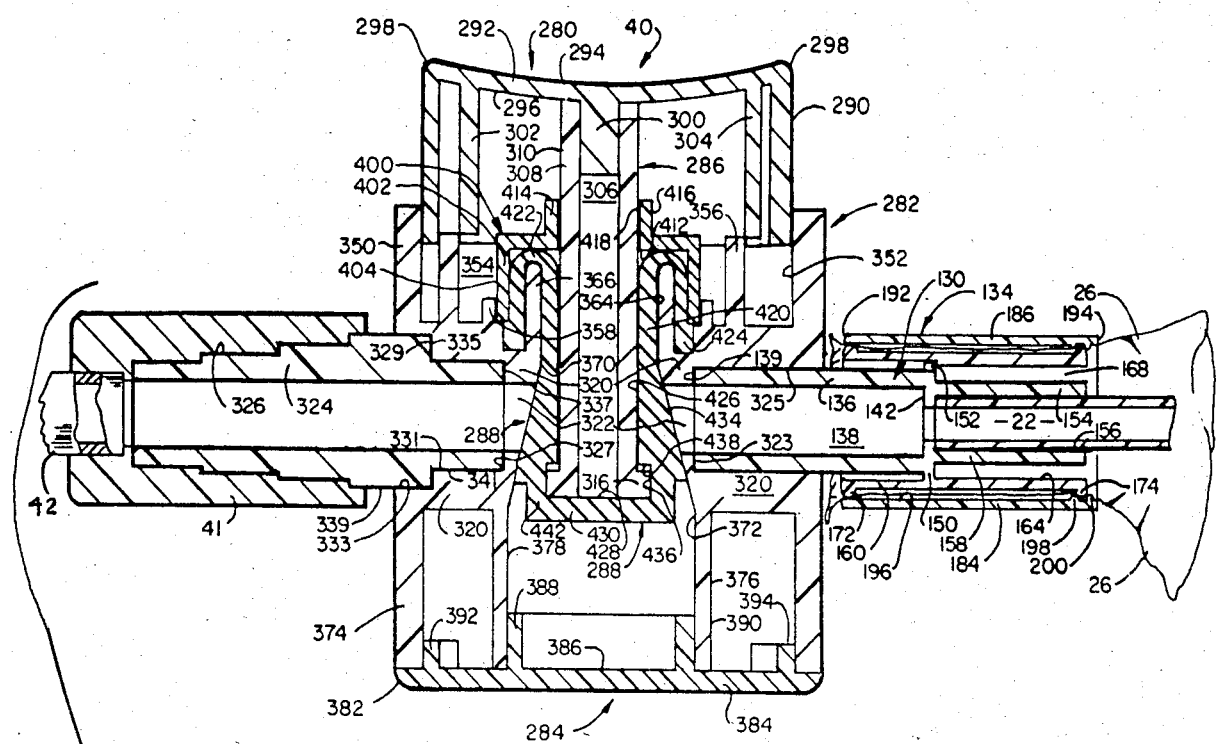
FIG. 3
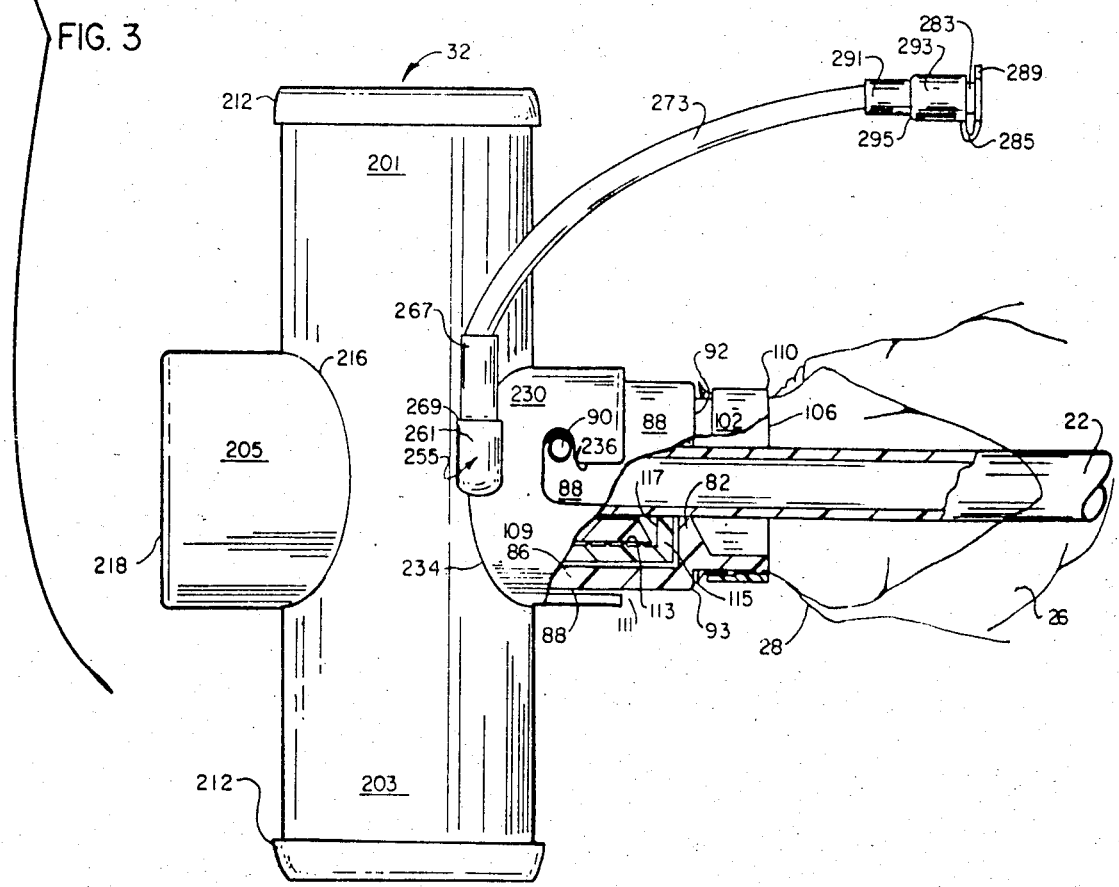

ASPIRATING/VENTILATING APPARATUS AND METHOD

CONTINUITY

The application is a division of U.S. patent application Ser. No. 633,570, filing July 23, 1984, now U.S. Pat. No. 4,569,344, issued Feb. 11, 1986.

FIELD OF INVENTION

The present invention relates broadly to machine ventilation of the respiratory system of a medical patient and selected evacuation of accumulated fluids from within the trachea/bronchi of the patient, and, more particularly to a single novel apparatus (and related method) for conjointly so ventilating and selectively aspirating the respiratory system of the patient.

PRIOR ART

Alternate use and successive removal of endotracheal tubes and fluid aspiratory tubes to sequentially respirate and aspirate the trachea and bronchi of a medical patient has fallen into disrupt because of several attending and well known disadvantages, not the least of which is patient trauma and risk. In lieu thereof, it has been proposed that a single coupling mechanism be connected to the patient for an essentially long term interval, which functions, selectively, to ventilate and aspirate. See U.S. Pat. No. 3,991,762.

However, such proposals have also suffered from serious drawbacks, including but not limited to being of relatively expensive and cumbersome components, capable of causing inadvertent aspiration, imposing torque upon the aspirating catheter tube, using potentially harmful mechanical manipulation of the catheter tube, capable of causing stress tearing of a sterile envelope around the catheter tube, presenting difficulty in assembling and disassembling and venting suction to the atmosphere during non-aspiration.

With the foregoing in mind, in brief summary, the present invention overcomes or substantially alleviates the problems of the prior art, mentioned abbreviatedly above, and comprises an apparatus (and related method) which integrates into a single unit the selective capacity to both involuntarily respirate a patient and aspirate fluids from a patient's trachea and bronchi. The apparatus, among other things, reduces trauma and risk, prevents inadvertent aspiration caused by either the attending nurse or the patient, prevents interruption of positive ventilating pressure by the existence and manipulation of the aspirating catheter tube, comprises relatively inexpensive, facile and reliable components, imposes only axial forces upon a flexible envelope (which surrounds and preserves the sterility of the catheter tube) and upon the catheter tube as well, does not mechanically manipulate the catheter tube, is easily assembled and disassembled (in whole or in part—even when the apparatus is connected to the patient) and which does not vent suction to the atmosphere when not aspirating.

Accordingly, it is a primary object of this invention to provide a novel ventilating and aspirating apparatus and method which overcome or substantially alleviate the problems of the prior art.

Another important object is the provision of a novel apparatus (and method) which integrates into a single unit the selective capacity to both involuntarily respirate a medical patient and aspirate fluids from the patient's trachea and bronchi.

Another significant object of the present invention is to provide a novel apparatus and method, of the type in question, which achieves one or more of the following: reduces trauma and risks, prevents inadvertent aspiration caused by either the attending nurse or the patient, prevents interruption of positive ventilating pressure by the existence and manipulation of the aspirating catheter tube, comprises relatively inexpensive, facile and reliable components, imposes only axial forces upon a flexible envelope (which surrounds and preserves the sterility of the catheter tube) and upon the catheter tube as well, does not mechanically manipulate the catheter tube, is easily assembled and disassembled (in whole or in part—even when the apparatus is connected to the patient) and which does not vent suction to the atmosphere when not aspirating.

A further dominant object is the provision of a ventilating/aspirating mechanism which comprises a novel aspirating valve which may be locked against inadvertent actuation.

Another paramount object of this invention is the provision of an aspirating valve which comprise a novel spring/sealing member.

An additional object of significance is the provision of a novel ventilating/aspirating apparatus which is greatly simplified, highly reliable, easy to use, cost effective, contamination free, preserves sterility and is safe and effective in use.

These and other objects and features of the present invention will be apparent from the detailed description taken with reference to the accompanying drawings.

BRIEF DESCRIPTION OF THE DRAWINGS

FIG. 3 is similar to FIG. 2 showing the aspirating vacuum control valve in cross section and the ventilating fitting in fragmentary cross section;

DETAILED DESCRIPTION OF THE ILLUSTRATED EMBODIMENT

Figure 1:
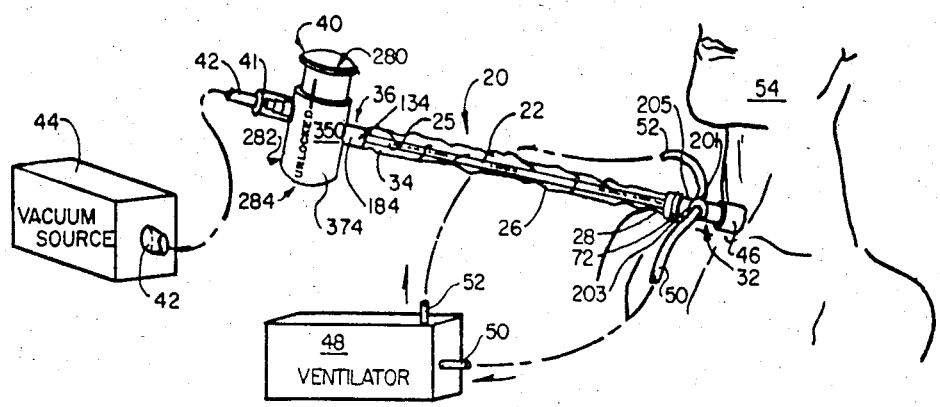
FIG. 1 is a perspective, with parts shown schematically, of a presently preferred ventilator/aspirator embodiment of the present invention, shown connected to a medical patient, as well as to a ventilator and a vacuum source.
Figure 2:
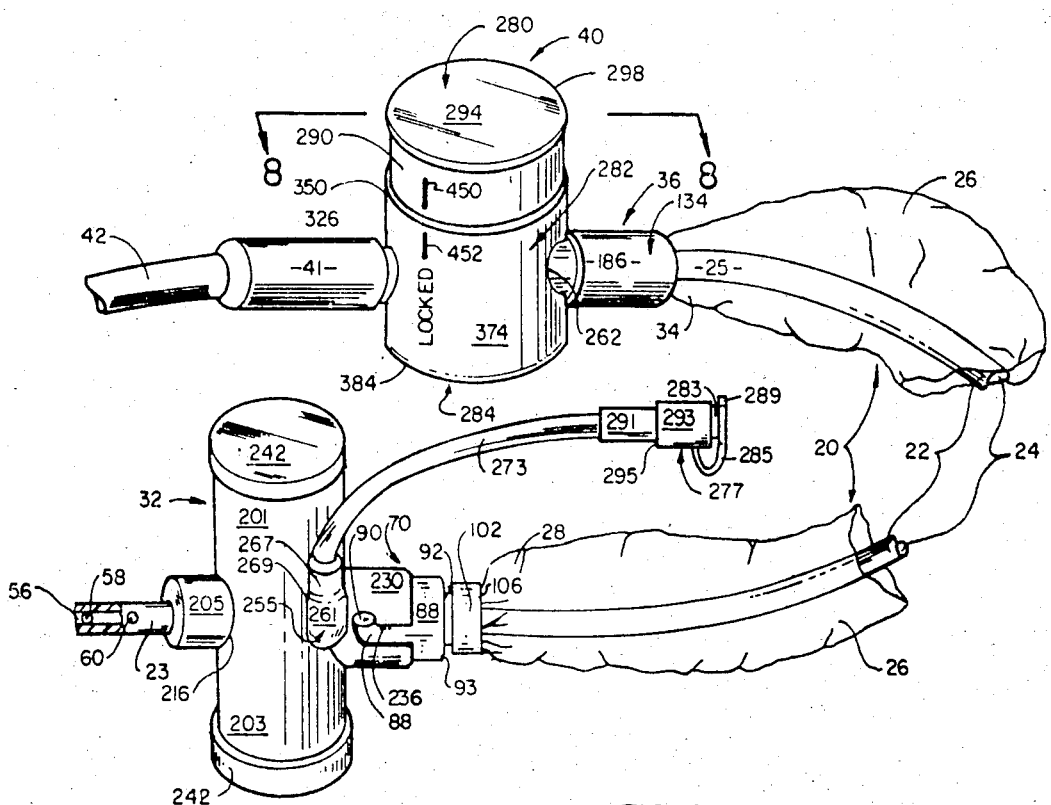
FIG. 2 is an enlarged perspective representation of the ventilator/aspirator mechanism of FIG. 1 with the control valve thereof in the unlocked, closed condition.

Reference is now made to the drawings wherein like numerals are used to designate like materials throughout. A presently preferred integrated ventilator/aspirator mechanism, generally designated 20 and implementing the provisions of the present invention, is best illustrated in FIGS. 1–3. Ventilating/aspirating mechanism 20 is illustrated as being connected to a medical patient in FIG. 1 at a tracheostomy connector 46 or an endotracheal tube and left indwelling for repeated use over a protracted interval of time. Mechanism 20 comprises a central portion comprising an interior sterile aspirating catheter tube 22 having a hollow interior passageway 24 of sufficient capacity to aspirate fluids from the trachea and bronchi. The aspirating catheter tube 22 is formed of suitable synthetic resinous material such as medical grade transparent polyvinyl chloride and further comprises an annular wall of essentially uniform thickness throughout and having an outside diameter selected to pass through the throat and into the lungs of the patient.

The aspirating catheter tube 22 has sufficient strength to prevent buckling, bending and twisting of the catheter tube which occludes or tends to occlude the catheter tube. The tube 22 is surrounded in sealed relation by a sterile sack or flexible envelope 26, formed of suitable impervious synthetic resinous film material of medical grade, such as polyethylene film in sleeve form. The flexible envelope 26 is selectively detachable at each end as explained herein and allows ready manual manipulation of the catheter tube 22 disposed therein as hereinafter more fully explained. The catheter tube 22 is controlled solely by manual manipulation thereof through the envelope and is at no time subject to mechanical manipulation. Also it is preferred that catheter tube 22 be radiopaque to facilitate location thereof in the patient by use of X-ray techniques.

The distal end 23 of the aspirating catheter tube 22 comprises, as illustrated, three openings, i.e. the axial opening 56 at the tip and two radially disposed apertures 58 and 60 in the wall of the catheter tube. See FIG. 2.

The flexible film envelope 26 comprises a first end 28 (FIG. 4), which, in the assembled condition, is secured in tight sealing though releasable relation against inadvertent separation at a linear force fit coupling, generally designated 30. Coupling 30 is releasably secured to a ventilating Tee or Cross fitting, generally designated 32. The distal end 23 of the catheter tube 22 slidably passes through both the coupling 30 and the ventilating fitting 32 in sealed relation, in a manner and for purposes hereinafter more fully explained.

The flexible envelope 26 comprises a second end 34 (FIG. 5) which is, in the assembled condition, snugly, releasably and sealingly secured to a linear force fit coupling, generally designated 36, against inadvertent removal. The proximal end 25 of the aspirating cathether tube 22 is permanently anchored, adhesively or in some other suitable way, to the valve coupling 36. Coupling 36 is associated with an aspirating vacuum control valve, generally designated 40, in a manner and for purposes more fully explained herein.

With particular reference to FIG. 1, it is to be noted that the aspirating vacuum control valve 40 is connected via an aspirating suction tube 42 to a vacuum source 44, e.g., a hospital suction system. FIG. 1 also illustrates the sealed attachment of the ventilating fitting 32 to the trachea tube connector 46, properly surgically placed into the throat of a patient. A ventilator 48, e.g., a hospital ventilating system, is connected to the ventilating fitting 32 via hollow delivery and exhaust tubes 50 and 52, respectively.

It is to be appreciated that a member of the hospital staff, e.g., a nurse or the like, can advance the catheter tube 22 into the throat of the patient 54 by manually collapsing the flexible envelope 26 between the thumb and fore-finger of one hand upon the cathether tube and advancing the two, which causes the envelope to gather in an accordion fashion. The other hand is used to grip and thereby stabilize the position of the fitting 32. When the distal end 23 of the catheter tube is properly disposed within the patient, the nurse manually depresses the aspirating control valve 40 to cause undesirable fluids within the respiratory system of the patient 54 to be removed under the force of the vacuum of source 44 along the aspirating catheter tube 22.

Figure 4:
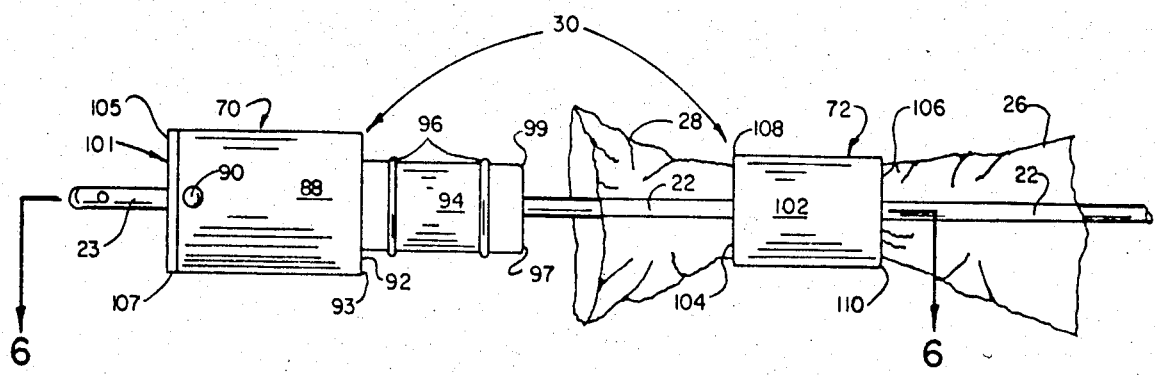
FIG. 4 is an exploded side elevational view depicting the manner in which the sterile flexible envelope is secured at one end thereof to a force-fit coupling associated with the ventilating fitting.
Figure 6:
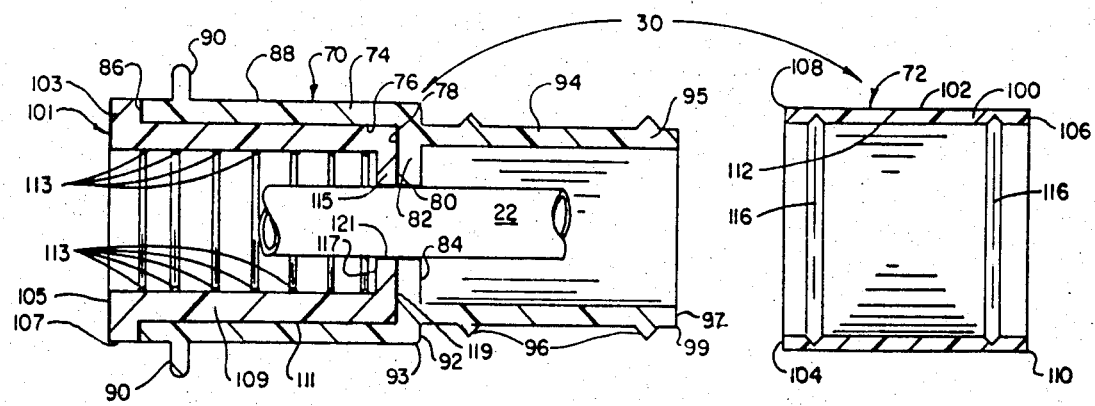
FIG. 6 is a cross section taken along lines 6—6 of FIG. 4, with the flexible envelope removed for clarity.

With particular reference to FIGS. 4 and 6, coupling 30 comprises two force-fit components, i.e., a stepped adapter, generally designated 70 and a sleeve, generally designated 72. The adapter 70 and the sleeve 72 are formed of suitable shape retaining synthetic resinous material, such as polypropylene.

The male adapter 70 is preferably formed as one piece by suitable molding techniques and comprises a generally annular body 74, which has a stepped interior comprising a relatively large annular bore 76 of uniform diameter, which merges with and terminates at an inside shoulder 78. An aperture 80 is disposed in central interior wall or flange 82 and has a relatively small diameter substantially equal to the outside diameter of the aspirating catheter tube 22. The wall 82 comprises a radially extending, generally exposed flat surface 84. The body 74 also comprises a blunt end in the nature of an annular flat edge face 86, disposed in a radial plane. The body 74 further comprises a cylindrical exterior face 88, which is interrupted adjacent edge 86 by two radially projecting and oppositely directed exterior cylindrical posts 90. Face 88 merges with a radially directed annular face 92 at annular rounded corner 93. Shoulder or face 92 in turn merges with a reduced diameter annular face 94 comprising part of a wall 95. Annular face 94 is interrupted by two spaced, triangular-shaped locking rings 96. Wall 95 comprises an edge 97, which merges with surface 94 at rounded annular corner 99.

It should be clear from inspection of FIG. 6 that the aspirating catheter tube 22 fits snugly within the bore 80 of adapter 70.

As shown in FIG. 6, the illustrated embodiment 20 comprises a cup-shaped insert seal, generally designated 101. Seal 101 is preferably formed from pliant urethane, or other suitable synthetic resinous material as one piece through conventional resin molding techniques. Seal 101 has the general appearance of a top hat and is sized and shaped to fit snugly against radial wall 86, internal annular surface 76 and radial shoulder 78. More specifically, one smooth side 99 of a radially directed flange 103 is contiguous with radial face 86. Thus, the flange 103 has a second smooth side 105, parallel to side 99, and an exposed annular surface 107. Surface 103 snugly engages the fitting 32 so that a tight static seal is created between flange 103, fitting 32 and adapter 70.

The flange 103 integrally merges with a thin wall central cylindrical portion 109, which has a longitudinal length essentially the same as the longitudinal or axial length of the annular surface 76. The cylindrical portion 109 has an outside annular surface 111, the diameter of which is such that a snug, contiguous and sealed relationship between surfaces 76 and 107 exists in the assembled condition. The interior surface of the cylindrical wall 109 is serrated at 113. The serrations are pulling rings and are only a molding aid.

Cylindrical wall 109 integrally merges with an interior radially directed wall 115. Wall 115 is illustrated as being of uniform thickness and as comprising a radial surface 117, which merges with serrated surface 113, and a radial surface 119 which is sealingly contiguous with shoulder surface 78.

Wall 115 has a central aperture 121, the diameter of which is no greater and preferably slightly less than the outside diameter of the catheter tube 22. Thus, a static and dynamic seal is created between the wall 115 and the catheter tube 22 at aperture 119. Accordingly, displacement, including but not limited to reciprocation, of catheter tube 22 will cause the wall 115 to wipe the exterior surface of the catheter tube clean and the mentioned seals prevent leakage across seal member 101 of ventilating pressure occurring within the fitting 32.

The female sleeve 72, preferably formed of polypropylene, comprises a generally annular body wall 100 having a smooth uninterrupted exterior annular surface 102 of uniform diameter. The annular exterior surface 102 merges, fore and aft, with flat edge surfaces 104 and 106 at rounded annular corners 108 and 110, respectively. Edges 104 and 106 merge with the interior of the sleeve 72. Interior face 112 of sleeve 72 accommodates displacement of the ring 72 over annular projection 95 of the adapter 70 during assembly. Face 112 comprises a generally annular interior bore having a smooth surface and a diameter slightly greater than the diameter of the annular face 94 of the adapter 70. The annular bore 112 is interrupted twice in the central portion thereof by V-shaped annular grooves 116, which are sized, shaped and located so as to linearly receive the wedge or triangle-shaped projection 96 of the adapter 70 in press fit relation to assemble the coupling 30, with the flexible envelope 26 interposed between the projections 96 and the grooves 116. Thus, annular line seals and common annular line compressive clamp forces on both the inside and outside surfaces of the envelope are created. As a consequence, bacteria and other contaminates are prevented from entering the flexible envelope. Exclusive of the indwelling fitting 32, the remainder of the mechanism may be removed and replaced by a like mechanism by simply removing the coupling 30 from its releasable connection to the fitting 32.

Figure 5:
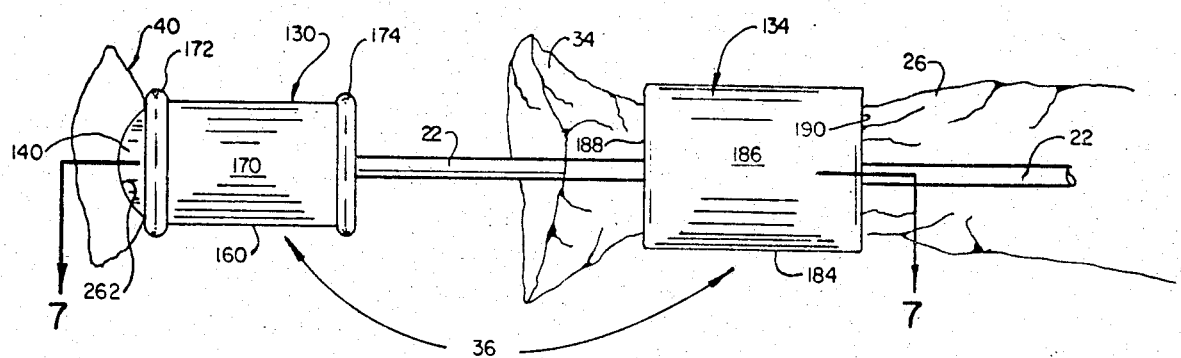
FIG. 5 is an exploded side elevation illustrating a force-fit coupling by which the flexible envelope is secured to the aspirating vacuum control valve.
Figure 7:
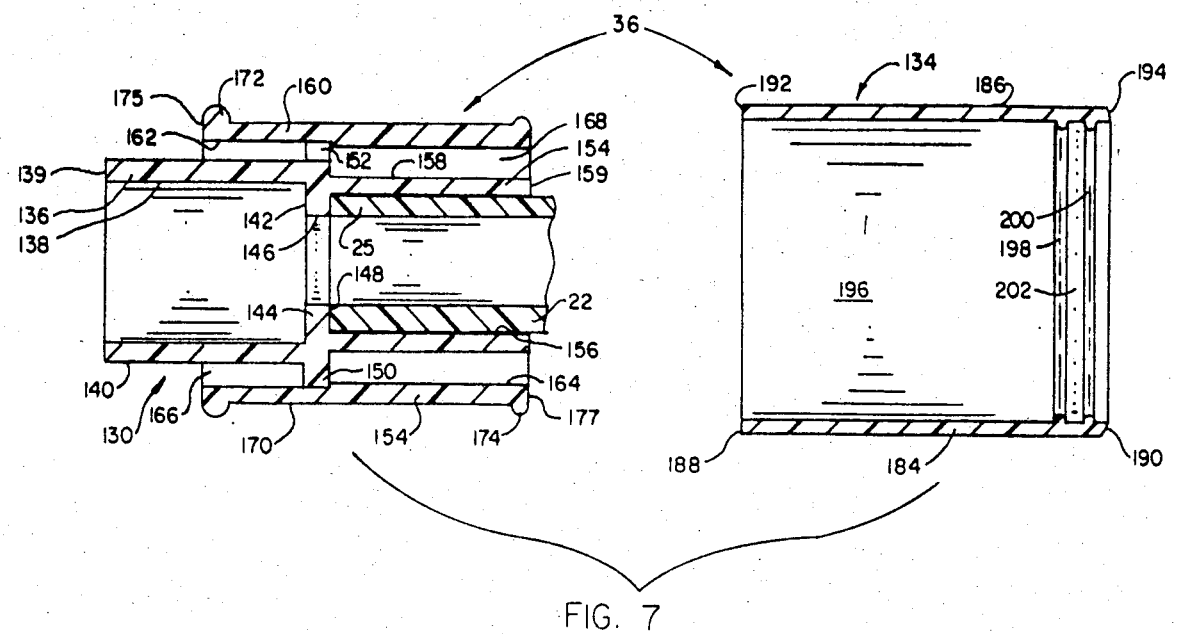
FIG. 7 is a cross section taken along lines 7—7 of FIG. 5, with the flexible envelope removed for clarity.

Reference is now made to FIGS. 5 and 7 for further detail concerning coupling 36. Coupling 36 comprises a male adapter, generally designated 130 and a female sleeve, generally designated 134. Each of the parts 130 and 134 is formed of a suitable synthetic resinous material, preferably polypropylene.

The adapter 130 comprises an annular wall 136. The annular wall 136 comprises an interior cylindrical smooth bore 138 of uniform diameter. The wall 136 fits tightly into a bore in valve 40 as hereinafter more fully esplained and is secured in said position by a suitable adhesive. Wall 136 terminates in radial edge 139. Wall 136 also comprises an exterior cylindrical smooth surface 140. The interior bore 136 terminates at step or shoulder 142. Shoulder 142 is a flat radial surface of an inwardly directed annular wall 144. Wall 144 has a reduced diameter central bore 146 having the same diameter as the interior bore of the catheter tube 22. Wall 144 provides a further flat shoulder 148 against which one edge of the aspirating catheter tube 22 (at end 25) abuts.

The exterior cylindrical surface 140 terminates in an outwardly directed radial bridge or web 150, which is integral with the previously described inwardly directed flange or wall 144. Web 150 has disposed therein a plurality of apertures 152, so that both sides of bridge or web 150 are at atmospheric pressure. Radial bridge 150 merges with an annular cantilevered inside wall 154, which projects away from the valve 40 coaxial of the end 25 of the aspirating catheter tube 22. Annular wall 54 comprises an interior annular smooth surface 156 having a uniform diameter substantially the same as the outside diameter of the catheter tube 22. A suitable adhesive preferably is applied to surface 156 to anchor and seal the exterior surface of the end 25 of the catheter tube 22 in the position illustrated in FIG. 7 against inadvertent or intentional removal or loss of vacuum pressure. Note that the blunt edge of the catheter tube end 25 abutts the wall 144 and that the inside diameter of the catheter tube and the aperture 146 are substantially the same. The annular wall 154 comprises an exterior smooth annular surface 158 of uniform diameter and a blunt radial edge 159.

Radial bridge 150, as shown, is also integral with a generally annular wall 160, which runs about two-thirds of the axial length of the adapter 130 and concentrically surrounds all of annular wall 154 and about one-half the axial length of the annular wall 136. Wall 160 comprises two spaced interior cylindrical surfaces 162 and 164 having the same uniform diameter. Surfaces 162 and 164 are interrupted by bridge 150. The diameter of walls 162 and 164 is greater than the respective diameters of wall surfaces 140 and 158, whereby annular grooves 166 and 168 are created. The wall 160 comprises an exterior annular generally smooth surface 170 which is interrupted by two annular projections 172 and 174, respectively, located near the end edges 175 and 177 of the wall 160.

From the foregoing, it should be readily apparent that the wall 160 comprises two oppositely directed cantilevered sections, which are supported centrally by the bridge 150 and, therefore, are substantially yieldable and allow linear force fit reception of the sleeve 134 with the end 34 of the envelope 26 interposed therebetween, as hereinafter more fully explained.

The sleeve 134 comprises an annular wall 184. Wall 184 has a smooth cylindrical exterior surface 186 of uniform diameter, which merges into radially directed flat edges 188 and 190, at corners 192 and 194. The wall 184 also comprises a cylindrical smooth interior surface 196. Adjacent edge 190, the smooth cylindrical interior 196 is interrupted by two internally directed annular radial projections 198 and 200, which are separated by an annular groove 202.

The diameter of the cylindrical surface 196 is selected to be substantially the same as the diameter of the projection 172 of the adapter 130, while the diameter of the projections 198 and 200 are slightly less than the diameter of the projection 174 of the adapter 130. Thus, the projection 194 may be linearly force-fit into the groove 202 of the sleeve 134, with the end 34 of the envelope 26 interposed between the projections 174, 198 and 200. As a consequence, the flexible envelope 26 is sealed at its inside and outside surfaces along two closely spaced common annular line seals and line clamps against bacterial entry.

Figure 10:
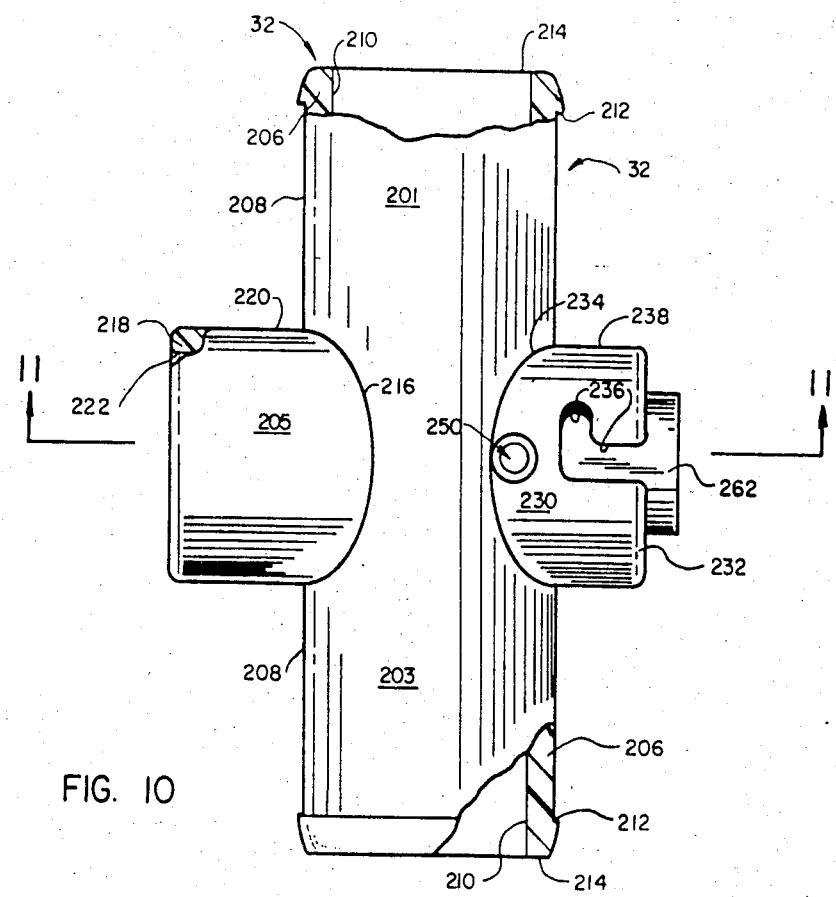
FIG. 10 is a side elevational view of the ventilating fitting, with parts thereof illustrated in cross section.
Figure 11:
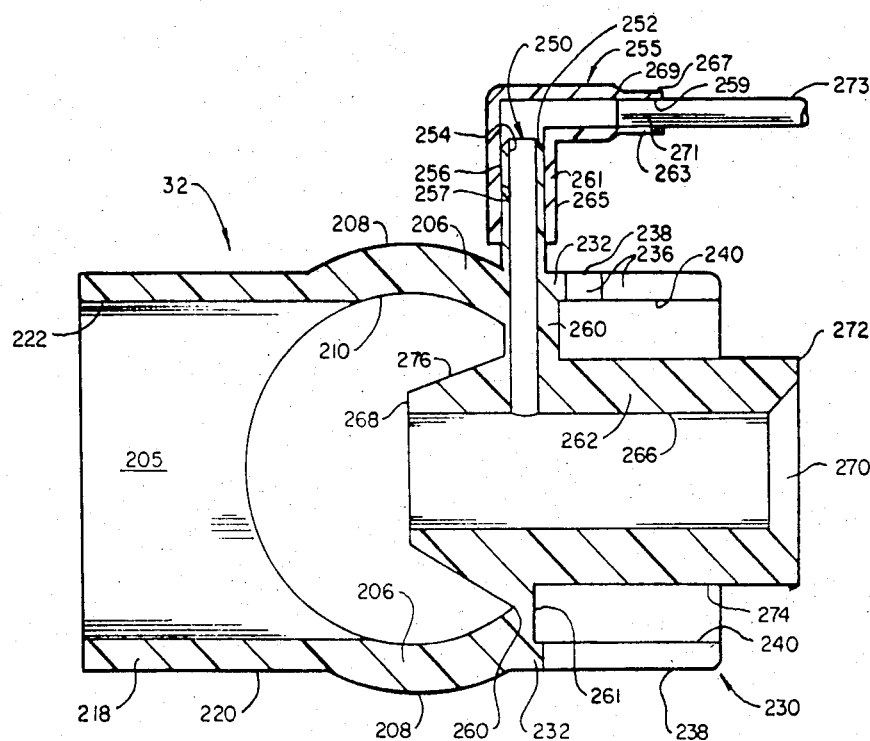
FIG. 11 is a cross section taken along lines 11—11 of FIG. 10.

With specific reference to FIGS. 10 and 11, a detailed description of the ventilating fitting 32 will ensue. Fitting 32 is preferably formed as one piece from suitable shape-retaining synthetic resinous material, preferably polypropylene. Fitting 32 generally comprises a hollow cross (or ventilating Tee which services ventilation needs). Two of the four ports service aspiration needs. Fitting 32 comprises first, second and third ventilating port structure 201, 203 and 205, respectively. Port 201, is integrally connected to the ventilator discharge tube 52 (FIG. 1), the port structure 203 is integrally connected to the ventilator return tube 50 (FIG. 1), and the port structure 205 is associated with a tracheostomy connector of a tracheal tube surgically placed within the patient.

Port structure 201 comprises a cylindrical wall 206, having a smooth cylindrical exterior 208, a smooth cylindrical interior 210 and an annular projection 212 adjacent the radial edge 214 to accommodate a press fit air-tight union with one end of the ventilator tube 52.

Port structure 203 is identical to, a continuation of and integral with port structure 201, although of opposite hand, and has been correspondingly designated with numerals heretofore mentioned. The cylindrical interior surface 210 constitutes a throughbore of uniform diameter extending between the annular edge 214 of the port structure 201 and the annular edge 214 of the port structure 203. Annular exterior projection 212 of the port structure 203 accommodates a press fit air-tight union with one end of the ventilator tube 50 (FIG. 1).

Port structure 205 is integral at interface line 216 with the wall 206 forming port structures 201 and 203. Port structure 205 comprises a cylindrical wall 218 of uniform thickness through defining an exterior cylindrical smooth surface 220 and an interior cylindrical bore wall surface 222, which opens into and thus communicates with the continuous bore 210 of the port structures 201 and 203. Accordingly, when the ventilator 48 is functioning, ventilating oxygenated air is displaced along tube 52 from ventilator 48 through the bore 210 of the port structure 201 and thence along the bore 220 of the port structure 205 into the lungs of the patient. During this phase, air flow along tube 50 is prohibited by ventilator 48. After a predetermined time sufficient to allow the lungs to be adequately expanded, displacement of air from ventilator 48 through tube 52 to the lungs of the patient 54 is discontinued and air from within the lungs of the patient is evacuated via bore 222 of port structure 205 and bore 210 of port structure 203 and exhaust tube 50 to the ventilator 48.

The fitting 32 also comprises port structure 230 which is generally axially aligned with port structure 205 and comprises two concentrically disposed cantilevered annular walls. Port structure 230 comprises an exterior, generally cylindrical annular cantilevered wall 232, which integrally merges with the previously described wall 206 along arcuate interface 234 (FIG. 10).

The outside annular wall 232 is interrupted axially and transversely by oppositely located L-shaped slots 236 into which the previously described posts 90 of the coupling 30 are tightly inserted and releasably locked when in the assembled position, as shown in FIGS. 2 and 3. The exterior cylindrical surface 238 is smooth, has a diameter substantially the same as the diameter of the cylindrical surface 220 of the port structure 205 and is aligned therewith. The interior cylindrical surface 240 of wall 232 comprises a diameter slightly less than the maximum transverse dimension of surface 88 of the adapter 70 so that the adapter 70 at surface 88 fits comfortably inside of the wall 232, in the assembled condition. In the assembled condition, the surface 105 of flange 103 of the cup-shaped seal 101 sealingly and contiguously engages surface 261 of fitting 32.

The wall 232 is further interrupted by transversely directed irrigation port structure 250. Irrigation port structure 250 comprises a cylindrical wall 252 integral with the wall 232 but projecting radially outward therefrom a substantial distance for ready access. Irrigation port wall 252 comprises an interior smooth bore 254 of uniform diameter and an exterior cylindrical smooth surface 256 of uniform diameter. Radial bore 254 continues through the wall 232 and into fluid communication with the hollow interior of the fitting 32, in a fashion and for a purpose yet to be explained.

Bore 252 passes through a cylindrical interior radial rib 260 of material integrally located inside of cylindrical rib or wall 232. Interior cylindrical wall 260 merges in transverse relation with previously mentioned cylindrical wall or annulus 262. The wall 260 comprises annular surface 261. Interior annulus 262 is generally concentrically disposed within cylindrical wall 232. Cylindrical wall 262 comprises an interior bore 266 having a diameter substantially the same as the outside diameter of the catheter tube 22 so that a snug seal exists when the catheter tube is located within and or displaced through the bore 266. Thus, ventilating pressure and oxygenated air are not lost across surface 266. Such displacement accommodates insertion of the aspirating catheter tube 22 into and removal of the catheter tube 22 from the lungs of the patient 54.

The cylindrical bore 266 terminates at the center of the transverse ventilating bore 210 at flat edge 268. The bore 266 also merges with beveled surface 270 at the exposed end of port structure 230. Beveled face 270 merges with transverse flat edge 272.

The cylindrical wall 262 extends from the center of the fitting 32 coaxially with wall 232 along the port structure 230 to a location beyond wall 232 and comprises a generally cylindrical exterior smooth surface 274 which merges with the exposed edge 272 and an inwardly divergent tapered or beveled annular surface 276 which merges with the edge 268. Surfaces 276 and 274 integrally merge with the annular connector or radial web 260.

The outside diameter of the surface 274 is such that the adapter 70 at interior bore surface 76 slides snugly over cylindrical surface 274 as the posts 90 are inserted into the L-shaped slots 236 and rotated to releasably secure the coupling 30 to the fitting 32, in the assembled condition.

The irrigation bore 254, of relatively small diameter, passes through the rib 260 and the wall 262 to intersect in fluid communication with the catheter tube bore 66 such that irrigating fluid introduced through bore 254 may be used to wash the exterior of the catheter tube as desired, particularly during withdrawal. This is helpful in unclogging and/or clearing the catheter tube ports 56, 58 and 60 at the distal end 23 of the catheter tube 22. Introduction of solution into the lungs helps break up lung secretions. The irrigating solution is vented from the apparatus 20 to the ventilator 48 and to the vacuum source 44 (FIG. 1) via ventilator return tube 50 and the interior of the catheter tube 22, respectively.

To faciliate introduction of irrigation solution at port 254, the projecting annular wall 252 associated therewith is a recipient of a press fit elastomeric elbow 255. The elbow 255 is formed of highly elastic although shape retaining material and comprises two interior bores 257 and 259, which are of the same diameter and intersect at 90°. Elbow 255 comprises a generally cylindrical wall 261 along the short leg of the elbow and a substantially cylindrical wall 263 along the longer of the two legs. The outside cylindrical surface 265 of leg wall 261 is of a slightly greater diameter than the outside diameter of the cylindrial surface 267 of the longer leg wall 263. The wall 263 is stepped at annular site 269 to a slightly greater thickness.

The elbow 255 is formed of a material, such as soft, yieldable molded vinyl so that it may be stretched readily, but tends to return to its original shape by reason of the memory of the material from which the elbow 255 is formed. Thus, leg wall 261 may be readily expanded as it is axially force-fit over the annular valve wall 252 to achieve the position illustrated in FIG. 11. The force of the memory from which elbow 255 is formed retains the elbow in said force-fit position.

By the same token, the proximal end 271 of an irrigation tube 273, having an outside diameter slightly greater than the inside diameter 259 may be readily manually inserted into the longer leg wall 263 and adhesively secured at said location, if desired. (See FIG. 11.)

Figure 12:
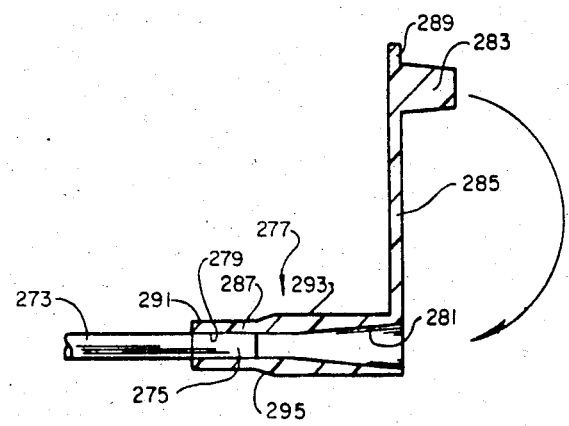
FIG. 12 is a cross sectional view of the influent irrigation fitting associated with the ventilating fitting of the mechanism of FIG. 1.

The end 275 of the irrigation tube 273 is secured to a hub adapter, generally designated 277 (FIG. 12). Hub adapter is preferably formed of the same material as elbow 255. More specifically, the distal end 275 of the irrigation tube 273 is inserted into the slightly smaller interior bore 279 of the hub and retained at said location by a suitable adhesive or the like. The bore 279 is conically enlarged at site 281 to accommodate receipt of a syringe or a fitting associated with a source of irrigation fluid, when the aspirating catheter tube 22 is being irrigated.

When irrigation is not occurring, a correspondingly shaped plug 283 is tightly, although releasably inserted into the conical bore 281 to prevent entry of undesired and/or unsterile substances. The tapered plug 283 is connected to an integral tether 285 molded as one piece with a generally cylindrial hub wall 287. The tether 285 is essentially rectangular in its configuration. Plug 283 is also connected to a cantilevered lip 289, which may be manually grasped and pulled to remove the plug 283 from the tapered port 281 when irrigation is to occur.

The generally cylindrical wall 287 comprises an exposed cylindrical exterior surface 291 which merges with a slightly larger diameter cylindrical surface 293, at step or shoulder 295.

It is to be appreciated, as illustrated in FIG. 2 that during periods of storage and prior to connecting the aspirating/ventilating apparatus 20 to the patient (as illustrated in FIG. 1), all or some of the three ventilating ports may be closed by use of a plastic force fit cap 242 (FIG. 2).

Reference is now made to the illustrations of aspirating vacuum control valve 40 for purposes of a more detailed description thereof. Broadly, in respect to FIGS. 3, 8 and 9, valve 40 comprises a manual button or valve actuator, generally designated 280, a main valve body, generally designated 282, a bottom end closure, generally designated 284, a plunger, generally designated 286 and a cup-shaped seal member, generally designated 288. All said parts, except for seal member 288, are preferably formed of one piece mold construction from a suitable rigid, shape retaining synthetic resinous material. ABS is preferred because it accommodates solvent bonding.

The manual actuator 280 is generally of an inverted cupshape configuration. The inverted cup-shaped actuator 280 is defined by an essentially oval downwardly directed continuous flange 290 and a concave actuator wall 292, which comprises an exposed concave oval surface 294. Concave wall 292 is of uniform thickness and comprises an interior surface 296 and is integrally connected to the oval flange 290 along a rounded oval 90° corner 298.

The actuator 280 also comprises a centrally disposed downwardly projecting relatively short cylindrical post 300, used to unite the actuator 280 to the plunger 286. Post 300 is integral with the wall 292.

Also integral with the wall 292 are two elongated cylindrical posts 302 and 304, each of which has a length only slightly less than the length of the flange 290. Cylindrical post 302 and 304 accommodate depression of the actuator 280 when the valve 40 is unlocked and, when the valve 40 is placed in its "locked" position post 302 and 304 prevent either intentional or inadvertent depression of the actuator 280, in a manner hereinafter more fully explained.

The plunger 286 comprises a tubular piece having a central hollow cylindrical body 306, an annular wall 308, which defines a cylindrical bore 310. The diameter of bore 310 is substantially the same as the diameter of the post 300 of the actuator 280. Bore 310 allows air to escape fromthe interior of the sealing member 288 during assembly. As can be seen clearly from FIGS. 3, 8 and 9, in the assembled condition, the plunger bore 310 contiguously surrounds the cylindrical projection 300 and is caused to be integral therewith preferably by utilization of solvent bonding. The cylindrical or annular wall 308 merges with a radially or transversely directed lower annular flange 316, which assists in securing the plunger 286 to the sealing member 288, as hereinafter more fully explained.

Figure 8:
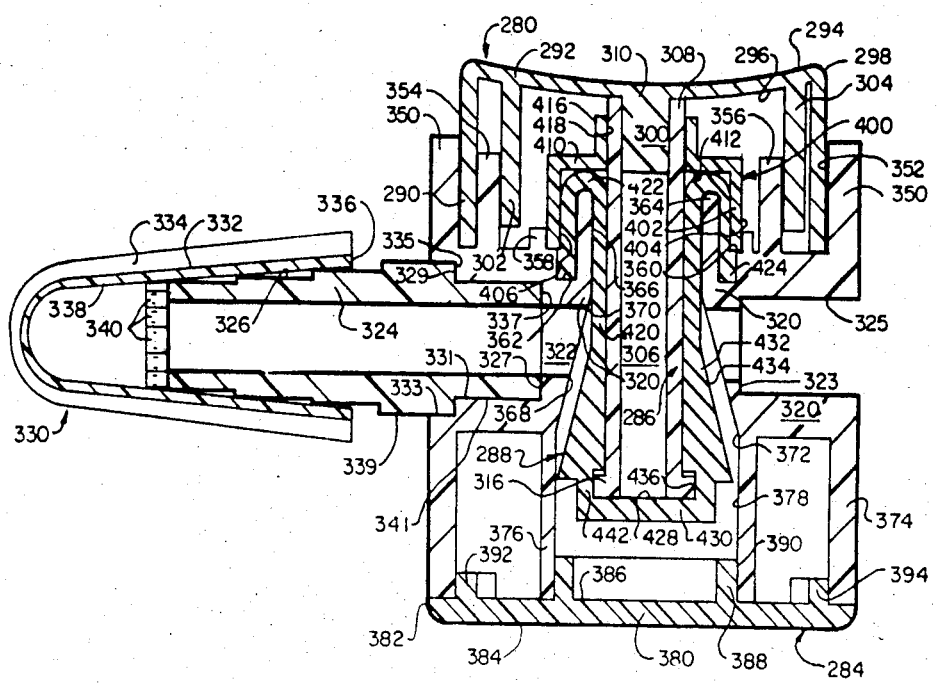
FIG. 8 is a further cross section of the valve of the mechanism of FIG. 1 taken along lines 8—8 thereof, the valve of FIG. 8 being in its unlocked, open condition.

The outside diameter of the annulus 308 of the plunger 286 is uniform and sized to accommodate selective reciprocation with the actuator 280 from the position of FIG. 3 to the position of FIG. 8, when the valve 40 is in the "unlocked" condition. The overall length of the plunger 286 and the location and size of the annular wall 308 and flange 316 cause the overall length of the plunger 286 to extend beyond the central vacuum bore of the valve 40, for purposes more fully described.

The stationary central valve body 282 of the aspirating vacuum control valve 40 comprises a central portion 320, which defines a central aspirating bore 322, which has a uniform diameter throughout. Bore 322 is stepped or enlarged both fore and aft. More specifically, bore 322 is enlarged at shoulder 323 to an enlarged bore 325, which opens at the exterior surface of the valve body 282. See FIG. 8, especially. The length and diameter of enlarged bore 325 corresponds essentially with the available length and the outside diameter of annular wall 136 of adapter 130. Wall 136 is fit snugly within the bore 325 until edge 139 contiguously engages shoulder 323. Conventional solvent bonding, at surface 140 of wall 136, preferably integrally unites adapter 130 with valve body 282. See FIG. 9.

In the other direction bore 322 is twice enlarged at spaced shoulders 327 and 329 to form enlarged bore segments 331 and 333, respectively. Bore segment 333 opens at the exterior surface of the valve body 282.

The bore 322 has a diameter preferably essentially the same as the diameter of the surface 138 of adapter 130.

Figure 9:
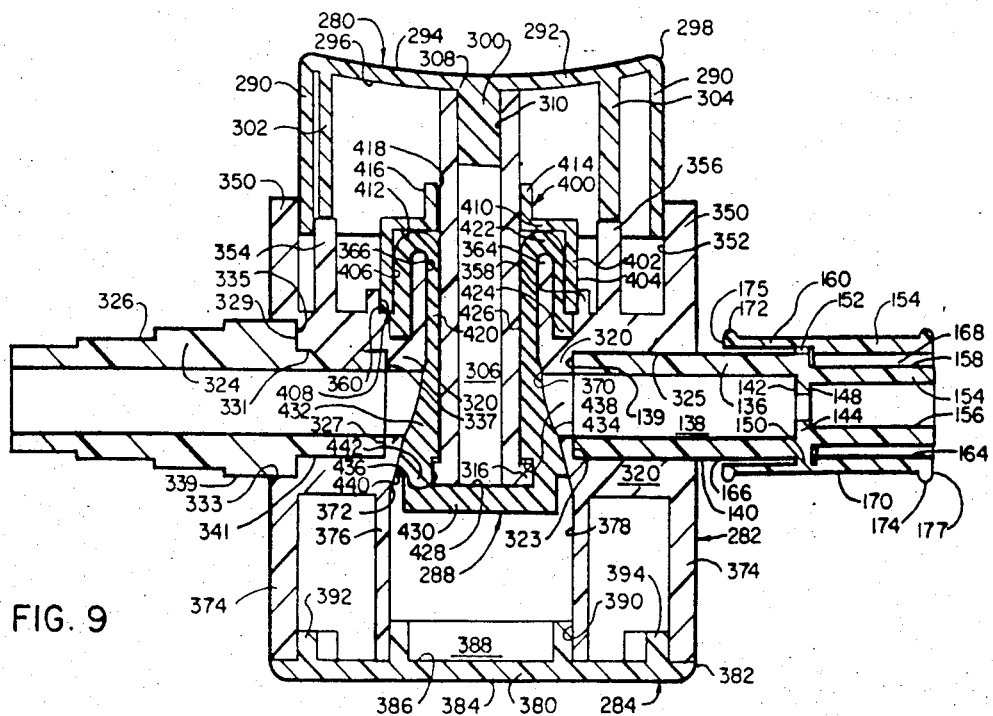
FIG. 9 is a cross section similar to FIG. 8 showing the valve in its locked, closed orientation.

Central valve portion 320 comprises an oppositely directed aspirating projection or generally annular wall 324, which has a stepped or serrated exposed exterior 326. The projection or annulus 324 is oppositely exteriorly stepped at shoulder 335 and end edge 337 to form cylindrical wall surfaces 339 and 341. Wall surfaces 339 and 341 together with shoulder 335 and edge 337 taken together corresponds in size, form and shape to the surfaces 331 and 333 and shoulders 327 and 329 and fit snugly therein when assembled. Conventional solvent bonding at edge 337, shoulder 335 and surfaces 339 and 341 integrally unites projection 324 with the valve body 282, as shown in FIGS. 3, 8 and 9.

Prior to installation of the mechanism 20, preferably the projection 324 is covered by a removable cap, generally designated 330 (FIG. 8). The illustrated removable cap 330 comprises a closed end wall 332 which connects to a central outwardly projecting flange 334. The wall 330 terminates in an annular edge 336, sized and shaped to come to rest adjacent the last enlarging step on the exposed surface 326 of the projection 324. The wall 332 is convergently, interiorly tapered at interior surface 338. In the illustrated configuration, the surface 338, along that portion which is contiguous with the projection 324 is shown as comprising a plurality of ribs 340, which assist in preventing inadvertent removal of the cap 330 from the position illustrated in FIG. 8, thereby preserving the sterility and preventing contamination of the projection 324 and the valve 40 during storage and prior to connection to the patient.

At the time of installation, the cap 330 is manually removed and connector sleeve 41 force fit over the hollow projection 324, as illustrated in FIG. 3. Connector sleeve 41 is also force fit over one end of the aspirating vacuum tube 42.

An upwardly directed oval shaped flange 350 comprises part of valve part 282 and is formed as one piece with central valve portion 320. The interior surface 352 of the upwardly directed flange 350 is spaced a very slight distance from the exterior surface of the actuator flange 290. Thus, when in the unlocked condition, the actuator 280 may be reciprocated up and down between the positions of FIGS. 3 and 8. The configuration of the flange 350 and its interior surface 352 closely matches the oval exterior configuration of the actuator flange 290.

A pair of upwardly directed cylindrical posts 354 and 356 project integrally from and are formed as one piece with central valve portion 320. The lengths of posts 354 and 356 are identical and, in the unlocked position, allow clearance of the actuator posts 302 and 304 across the tops of posts 354 and 356, during actuator reciprocation. The axial spacing between flange 350 and post 354 is substantially less than the axial spacing between the flange 350 and the post 356, so that a certain interference is caused in the locked condition between actuator post 304 and valve post 354 and between actuator post 302 and valve body post 356 to lock the valve 40 against actuation.

A relatively short annular wall 358 forms part of the valve part 282 and is molded as one piece with the central valve portion 320. Annular wall 358 is stepped at or has a shoulder or open groove 360 for purposes yet to be explained. The stepped annular interior of the wall 358 terminates in a blind bore base 362, which is recessed somewhat into central valve body 362. The base 362 of the blind bore emerges in an elongated upwardly directed annular wall 364 of smaller although uniform inside and outside diameters. The annular wall 364 projects upwardly a distance substantially beyond the distance traversed by the wall 358 but to a location beneath or lower than both the flange 350 and the posts 354 and 356. The plunger 286 is disposed within but is spaced a substantial distance from the interior bore 366 of the annular wall 364 so that plunger reciprocation is easily accommodated.

In a downward direction, the bore 366 of the annular wall 364 merges into a tapered valve seat bore 368. The conical seat 368 extends from the top of the central valve portion 320, at site 370, to the bottom of the central bottom valve portion 320, at site 372.

A downwardly extending exposed or exterior flange 374 also comprises the valve part 282 and is sized and shaped substantially identical to the previously mentioned flange 350, except flange 374 is downwardly directed. Flanges 350 and 374 merge with each other at both sides of the valve housing 282. Valve part 282 also comprises a downwardly directed interior annular wall 376, which is disposed interior of the flange 374. The downwardly directed length of wall 376 is equal to the length of the flange 374. The interior bore 378 of the annular wall 376 is of uniform diameter throughout and merges with the tapered valve seat surface 368 at annular site 372. The bore 378 is sized and of a sufficient length and diameter to accommodate reciprocation of the plunger 306 along with the surrounding seal member 288, which seal member will hereinafter be more fully described.

As mentioned, the aspirating vacuum control valve 40 comprises a bottom 284. Bottom 284 is preferably formed from a rigid, shape retaining synthetic resinous material. Bottom 284 comprises a wall 380 of substantially uniform thickness, defining an oval shaped edge 382, which matches flange 374, and a flat exposed bottom surface 384, which merges a rounded corner at edge 382. The upper surface 386 of bottom wall 386 merges with an integral upwardly directed central annulus 388, having a relatively short length. The exterior diameter of the wall 388 at surface 390 has a diameter substantially the same as the bore 378 so that the bottom 284 may be placed in the assembled position and there retained by either a force-fit relationship or by use of a suitable adhesive at the interface between the bore surface 378 and the wall surface 390.

The bottom 284 also comprises identical though opposite hand upwardly directed arcuate wall projections 392 and 394. Arcuate projections 392 are integral with wall 380, preferably formed as one piece therewith using conventional plastic molding techniques and are sized and shaped so as to be contiguous with the interior surface of the oval flange 374. Adhesive may be placed between the projections 392 and 394 and the flange 374 to better secure the valve bottom 284 in the assembled position.

With continued reference to FIGS. 3, 8 and 9, valve 40 also comprises a retainer/guide member, generally designated 400. Guide retainer member 400 comprises an annular wall 402, having a length substantially the same as the posts 354 and 356 and defining a cylindrical exterior surface 404 of uniform diameter and an interior bore 406 of uniform diameter. The exterior surface 404 of the wall 402 is contiguous with the interior surface of the annular wall 358 and is secured thereto, at site 408, by use of a suitable adhesive or the like.

The wall 404 merges with a transverse disc-shaped wall 410 having the same thickness as wall 402, but disposed at 90° thereto. Wall 410 defines a shoulder or step 412 adjacent the bore 406. The transverse wall 410 integrally merges with an annular wall 414, which projects upwardly, and has a thickness substantially the same as walls 402 and 410 and a length substantially less than the length of wall 402. Upwardly directed annular wall 414 comprises an exterior cylindrical surface 416 of uniform diameter and an interior bore at cylindrical surface 418, the diameter of which is slightly greater than the diameter of the central portion 306 of the plunger 286.

Thus, the fitting 400 and particularly the wall 414 thereof accommodates the previously mentioned reciprocation of plunger 286 and serves as a directional guide to maintain plunger alignment during such reciprocation.

The sealing member 288 is formed of a shape retaining, highly elastic substance such as synthetic rubber and functions not only to seal the aspirating bore 322 of the valve 40, when in the closed position, but also as a spring by which the actuator 280 is normally biased into its elevated, closed position of FIG. 3. To achieve this objective, the sealing member 288 is stretch fitted over the plunger 286 so as to be placed in a slight state of tension when disposed as illustrated in FIGS. 3 and 9 and in a substantially greater state of tension when in the position of FIG. 8, the material from which the sealing member 288 is fabricated having memory tending or attempting to restore the sealing member 288 to a state of no stress.

The sealing member 288 comprises a generally annular upper end portion 420 having a relatively thin wall section, the thickness thereof changing, depending upon the amount of tension imparted thereto at any particular point in time. The annular wall 420 is folded upon itself around the annular upper edge of annular wall 364 to form annular reverse curve 422 in the sealing member, whereby the direction of the central wall 420 is changed from upward to downward. Beyond the reverse curve 422, the annular wall 420 fits tightly between walls 364 and 402. The end of the annular wall 420 beyond the reverse curve terminates in an enlarged annular flange 424, which is snugly received in annular groove 362 in central valve body 320 and there retained by the union of wall 402 to annular wall 358 at annular groove site 360. By reason of the sealing member 288 being secured at flange 424 within the annular groove 362, stretch fit tension is applied to the sealing member without pulling the flange 424 from the groove 362.

Initially, during the assembly of the valve 40 with the bottom 284 and the actuator 280 not yet attached, the plunger 286 is inserted up through the hollow bore 426 of the annular sealing member wall 420. The plunger flange 316 is within annular slot 136 and engages contiguously the interior surface 428 of a bottom disc shaped wall 430. The plunger 386 is also caused to extend alignedly through the bore 418 of the annular guide wall 414. The reverse curve 422 is manually created with flange 424 being contiguous with the groove 362. The retainer 400 is installed as described. This creates a very low level of tension in the sealing member 288. The plunger 286 is thereafter connected to the actuator projection 300, at bore 310 as heretofore explained and the bottom 284 is attached.

The annular wall 420 of sealing member 288 merges in a downward direction with a thicker wall portion 432, the exterior surface 434 of which is conically shaped so as to correspond with the central valve body seat 368. The interior of wall portion 432 represents essentially a continuation of the interior bore 426, which is interrupted at the lower end thereof by an annular enlargement 436, which accommodates the plunger flange 316 and defines a shoulder 438. Shoulder 438 aids in preventing inadvertent upward displcement of the plunger flange 316 along the bore 426 as explained earlier.

The conical exterior surface 434 terminates at a shoulder 440. Shoulder 440 merges with a lower relatively short reduced diameter annular wall 442. Wall 442 is integral with the bottom wall 430 of the sealing member.

Thus, when no pressure is exerted upon the actuator 280 and the valve is in the unlocked position, the memory of the material from which the sealing member 288 is made will, pursuant to tensile stress disposed therein, urge the actuator 280 and the plunger 286 into the elevated position of FIG. 3, which causes the conical sealing surface 434 to sealingly engage the central valve body seat surface 268 thereby preventing aspiration notwithstanding the vacuum force generated by source 44 (FIG. 1).

However, because of the substantial elasticity of the sealing member 288, when the valve 40 is in the unlocked position, the medical attendant, nurse or the like, may readily aspirate fluids accumulating within the trachea and/or bronchi by properly manipulating the flexible envelope 26 so that the catheter tube 22 therein is properly inserted into the lungs of the patient, following which the actuator 280 is manually depressed counter to the memory of sealing member 288 causing the undesired fluids to be aspirated along the hollow interior 24 of the catheter tube 22 and along the valve bore 322. The described open condition of the unlocked valve is illustrated in FIG. 8.

On those occasions, when it is desired not to utilize the valve 40, valve 40 may be placed in the locked condition by merely slightly manually elevating the actuator 280 between two fingers and rotating the actuator 180° so that it assumes the position illustrated in FIG. 9. In this position, the central valve body posts 354 and 356 are in direct alignment with the actuator posts 304 and 302, respectively, as illustrated in FIG. 9, so that it is impossible to depress the actuator 280 so that surface 438 is retained in its sealed relation with the seat 368.

As shown in FIGS. 1 and 2, the actuator 280, at flange 290, has indicia 450, comprising an eccentric mark. When the valve actuator 280 is in the locked position, the indicia 450 will be aligned with indicia 452, comprising another mark affixed to valve housing 282. See FIG. 2. Next to the indicia 452, the word "LOCKED" is displayed. Thus, the medical attendant knows the valve 40 may not be actuated in the described condition.

When the valve actuator 280 is in the rotated and unlocked position of FIG. 8, the indicia 450 will be aligned with indicia 454, comprising another mark affixed to the other side of the valve housing 282. See FIG. 1. Next to the indicia 454, the word "UNLOCKED" is displayed. Thus, the medical attendant knows the valve 40 is ready to be manually actuated as the need arises.

The invention may be embodied in other specific forms without departing from the spirit or essential characteristics thereof. The present embodiment is therefore considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by U.S. Letters Patent is:

1. A method of manufacturing a ventilating/aspirating assembly comprising the steps of:
   assembling a manual aspirating control valve by placing a plunger in a closed end of an exteriorly tapered elastic seal member and placing the plunger/sealing member assembly within a tapered sealing bore of a valve body having an open top and an open bottom, folding a wall which comprises an open end of the sealing member upon itself in reverse curve orientation, anchoring and sealing said wall in said reverse curve orientation in stretch fit relation thereby biasing the sealing member into a closed sealing position by forces comprising the memory of the material from which the sealing member is made;
   placing a bottom closure and a top actuator upon the valve body following installation of the plunger/sealing member assembly;
   linearly force-fit connecting the distal and proximal ends of a sterility preserving flexible manually collapsible envelope respectively between a ventilating/aspirating fitting and the manual aspirating control valve;
   stationarily connecting the proximal end of an aspirating catheter tube to the aspirating control valve and slidably associating the distal end of the catheter tube with the ventilating/aspirating fitting.

* * * * *